(12) United States Patent
Warner et al.

(10) Patent No.: US 10,507,056 B2
(45) Date of Patent: Dec. 17, 2019

(54) SYSTEM AND METHOD FOR REPRESENTATION AND VISUALIZATION OF CATHETER APPLIED FORCE AND POWER

(71) Applicant: General Electric Company, Schenectady, NY (US)

(72) Inventors: Adrian F. Warner, Wauwatosa, WI (US); Claudio P. Mejia, Wauwatosa, WI (US); Daniel R. Schneidewend, Wauwatsoa, WI (US); Rodger F. Schmit, Wauwatosa, WI (US); Timothy P. Stiemke, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 505 days.

(21) Appl. No.: 14/872,740

(22) Filed: Oct. 1, 2015

(65) Prior Publication Data

US 2017/0095289 A1     Apr. 6, 2017

(51) Int. Cl.
*A61B 18/12*     (2006.01)
*A61B 18/14*     (2006.01)
(Continued)

(52) U.S. Cl.
CPC ........ *A61B 18/1492* (2013.01); *A61B 5/0422* (2013.01); *A61B 5/065* (2013.01);
(Continued)

(58) Field of Classification Search
CPC ............ A61B 18/1233; A61B 18/1492; A61B 2018/00577; A61B 2018/0066;
(Continued)

(56) References Cited

U.S. PATENT DOCUMENTS 5,383,874 A    1/1995 Jackson et al.
5,837,001 A   11/1998 Mackey
(Continued)

FOREIGN PATENT DOCUMENTS

CN     103027695     4/2013
EP       179413      1/1991
(Continued)

OTHER PUBLICATIONS

International Search Report and Written Opinion for corresponding PCT application No. PCT/US2016/052502 dated Dec. 9, 2016; 13 pages.

*Primary Examiner* — Daniel W Fowler
(74) *Attorney, Agent, or Firm* — Boyle Fredrickson, S.C.

(57) ABSTRACT

In the present invention, a system and method for determining the orthogonality and applied force vector of an ablation catheter includes the steps of providing an electrophysiology system including an RF generator, a processor operably connected to the RF generator, a display operably connected to the processor and an ablation catheter operably connected to the RF generator and the processor, the catheter including an ablation electrode disposed opposite the RF generator and a number of microelectrodes disposed on and electrically isolated from the ablation electrode, the processor configured to compare data signals obtained from the microelectrodes with one another to derive a difference value for each pair of data signals, obtaining data signals from the microelectrodes, comparing the data signals from microelectrode pairs to determine difference values and generating a visual representation on the display of the orthogonality and applied force vector of the ablation electrode using the difference values.

4 Claims, 3 Drawing Sheets

(51) Int. Cl.
*A61B 5/00* (2006.01)
*A61B 5/042* (2006.01)
*A61B 5/06* (2006.01)
*A61B 34/10* (2016.01)
*A61B 18/00* (2006.01)
*A61B 90/00* (2016.01)

(52) U.S. Cl.
CPC ........ *A61B 5/6852* (2013.01); *A61B 18/1233* (2013.01); *A61B 34/10* (2016.02); *A61B 2018/0066* (2013.01); *A61B 2018/00577* (2013.01); *A61B 2018/00839* (2013.01); *A61B 2018/00875* (2013.01); *A61B 2018/126* (2013.01); *A61B 2018/1467* (2013.01); *A61B 2034/105* (2016.02); *A61B 2090/065* (2016.02)

(58) Field of Classification Search
CPC .... A61B 2018/00875; A61B 2018/126; A61B 2018/1467; A61B 34/10; A61B 2034/105
See application file for complete search history.

(56) References Cited

U.S. PATENT DOCUMENTS

| | | | |
|---|---|---|---|
| 6,064,905 A | 5/2000 | Webster, Jr. et al. | |
| 6,264,653 B1* | 7/2001 | Falwell | A61B 18/1492 606/34 |
| 8,157,789 B2 | 4/2012 | Leo et al. | |
| 8,347,738 B2 | 1/2013 | Tung et al. | |
| 8,435,232 B2 | 5/2013 | Aeby et al. | |
| 8,532,738 B2 | 9/2013 | Zino | |
| 8,567,265 B2 | 10/2013 | Aeby et al. | |
| 8,641,705 B2 | 2/2014 | Leo et al. | |
| 8,876,817 B2 | 11/2014 | Avitall et al. | |
| 2001/0034501 A1* | 10/2001 | Tom | A61B 17/3207 604/67 |
| 2002/0183738 A1* | 12/2002 | Chee | A61B 17/282 606/41 |
| 2003/0181965 A1* | 9/2003 | Levy, Jr. | A61B 18/1485 607/101 |
| 2008/0243214 A1 | 10/2008 | Koblish | |
| 2010/0168557 A1 | 7/2010 | Deno et al. | |
| 2010/0331658 A1 | 12/2010 | Kim et al. | |
| 2011/0152856 A1* | 6/2011 | Govari | A61B 18/1492 606/34 |
| 2011/0270046 A1* | 11/2011 | Paul | A61B 5/065 600/300 |
| 2013/0123775 A1* | 5/2013 | Grunewald | A61B 18/1492 606/41 |
| 2013/0172784 A1 | 7/2013 | Kirschenman | |
| 2013/0190747 A1* | 7/2013 | Koblish | A61B 18/1492 606/33 |
| 2014/0012160 A1 | 1/2014 | Ghaffari et al. | |
| 2014/0180152 A1 | 6/2014 | Maskara et al. | |
| 2015/0133914 A1 | 5/2015 | Koblish | |

FOREIGN PATENT DOCUMENTS

| | | |
|---|---|---|
| EP | 2862537 A1 | 4/2015 |
| WO | 2013106557 | 7/2013 |
| WO | 20150130824 A1 | 9/2015 |

\* cited by examiner

SYSTEM AND METHOD FOR REPRESENTATION AND VISUALIZATION OF CATHETER APPLIED FORCE AND POWER

BACKGROUND OF INVENTION

The invention relates to a system and method for providing a representation on a display of the direction of force and power being applied via a catheter utilized in an invasive procedure, e.g., an ablation procedure.

In performing invasive cardiac catheterization procedures, such as ablation procedures, it is necessary to provide the clinician with various information on the catheter used in the procedure, including the force exerted on the catheter as well as a visual indication of the location of the ablation catheter tip relative to the tissue being treated. In many procedures these parameters of the catheter tip are determined utilizing electrodes disposed on the catheter adjacent the tip of the catheter that are used to sense the various parameters of the catheter relative to the tissue as the catheter is moved. These electrodes provide signals to a processor operably connected to the catheter that interprets the signals and provides an indication of the forces exerted on and the location of the catheter tip, and thus the ablation electrode disposed on the catheter tip relative to the tissue being treated.

Many different methods, structures and systems have been developed for the interpretation of these signals in order to provide an accurate and useful representation of the catheter tip and surrounding tissue. One such system and method is disclosed in U.S. Pat. No. 8,876,817, entitled "ELECTROPHYSIOLOGY SYSTEM AND METHODS", which is expressly incorporated herein by reference for all purposes. In this reference, an ablation catheter has a tissue ablation electrode and a plurality of microelectrodes distributed about the circumference of the tissue ablation electrode adjacent the tip of the catheter and electrically isolated therefrom. The plurality of microelectrodes defines a plurality of bipolar microelectrode pairs. A mapping processor connected to the microelectrodes is configured to acquire output signals from the bipolar microelectrode pairs, compare the output signals, and generate an output to a display to provide a clinician with a visual indication of an orientation of the tissue ablation electrode relative to the tissue, i.e., an indication of whether the tissue ablation electrode is in contact with the tissue.

In this system and method, the mapping processor can additionally utilize the signals from the microelectrodes to generate an electronic map of the tissue in which the catheter is positioned. This can enable the clinician utilizing the catheter to identify abnormal tissues within the tissue being mapped and/or examined.

However, while the representation on the display of the orientation of the electrode relative to the tissue is instructive in assisting the clinician in the performance of the procedure, it is desirable to be able to provide the clinician with a representation on the display that provides more information to the clinician than simply the structure of the tissue around the catheter, the orientation of the ablation electrode relative to the tissue or whether the ablation electrode is in contact with the tissue.

Accordingly, it is desirable to develop system and method for the determination of various parameters of the ablation catheter that enhances the information presented to the clinician based on the signals obtained from the microelectrodes on the catheter.

BRIEF DESCRIPTION OF THE INVENTION

There is a need or desire for an improved system and method for the determination of the orientation and contact of a catheter with the surrounding tissue. The above-mentioned drawbacks and needs are addressed by the invention embodiments in the following descriptions.

According to one exemplary aspect of the invention, a system and method is provided to present a uniform presentation relative to all known variants of force sensing, including specialist multipole ablation catheters, that illustrates both applied force and applied power in a manner such that a representation of the expected tissue transformation can be easily visualized. The ability to adapt multipole ablation catheters for applied force sensing is also within the scope of the invention.

According to another aspect of an exemplary embodiment of the invention, the system and method utilizes a catheter including a sequence of axial differential pairs a subset electrodes positioned thereon. The signals obtained by the pairs of electrodes are utilized in an equation that defines the orthogonality of the catheter relative to the tissue based on the signals. This determination of orthogonality in turn may be utilized by itself as a new noise-reduced signal to assist in the performance of the particular procedure, or as a detection process to define vector of greatest conduction in the tissue surrounding the catheter. This conduction vector may be a primary signal in its own right or can be utilized to selectively steer the clinician to position the catheter tip, i.e., the ablation electrode, at the region of greatest interest determined by the vector. This method is useful in identification of either new ablation targets or indicative of additional burn relative to a previously selected target close by.

According to yet another exemplary embodiment of the invention, the signals obtained by the microelectrodes that are used to provide the enhanced visualization and correlations of the data related to the applied user pressure exerted on the catheter tip and the applied energy to achieve tissue necrosis and disruption to the physiological conduction path. The system and method has the ability to record and process this multivariate data in multiple planes of tissue to enable a three dimensional (3D) visualization of the associated changes to the tissue pathology allowing the user to better characterize the result of the procedure being performed.

According to another exemplary embodiment of the invention, an electrophysiology system includes an RF generator, a processor operably connected to the RF generator and an ablation catheter operably connected to the RF generator and the processor, the catheter including an ablation electrode disposed opposite the RF generator and forming a tip of the ablation catheter and a number of microelectrodes disposed on and electrically isolated from the ablation electrode, wherein the processor is configured to compare data signals obtained from the microelectrodes with one another to derive a difference value for each pair of data signals and create a visual representation of a degree of orthogonality of the ablation electrode relative to tissue within which the ablation electrode is positioned.

According to still another exemplary embodiment of the invention, a method for determining the orthogonality and applied force vector of an ablation catheter, includes the steps of providing an electrophysiology system including an RF generator, a processor operably connected to the RF generator, a display operably connected to the processor and an ablation catheter operably connected to the RF generator and the processor, the catheter including an ablation electrode disposed opposite the RF generator and forming a tip of the ablation catheter and a number of microelectrodes disposed on and electrically isolated from the ablation electrode, the processor configured to compare data signals obtained from the microelectrodes with one another to derive a difference value for each pair of data signals; positioning the ablation electrode within the tissue to be ablated; obtaining data signals from the microelectrodes; comparing the data signals from microelectrode pairs to determine difference values; and generating a visual representation on the display of the orthogonality and applied force vector of the ablation electrode relative to the tissue using the difference values.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings.

DETAILED DESCRIPTION OF THE DRAWINGS

Figure 1:
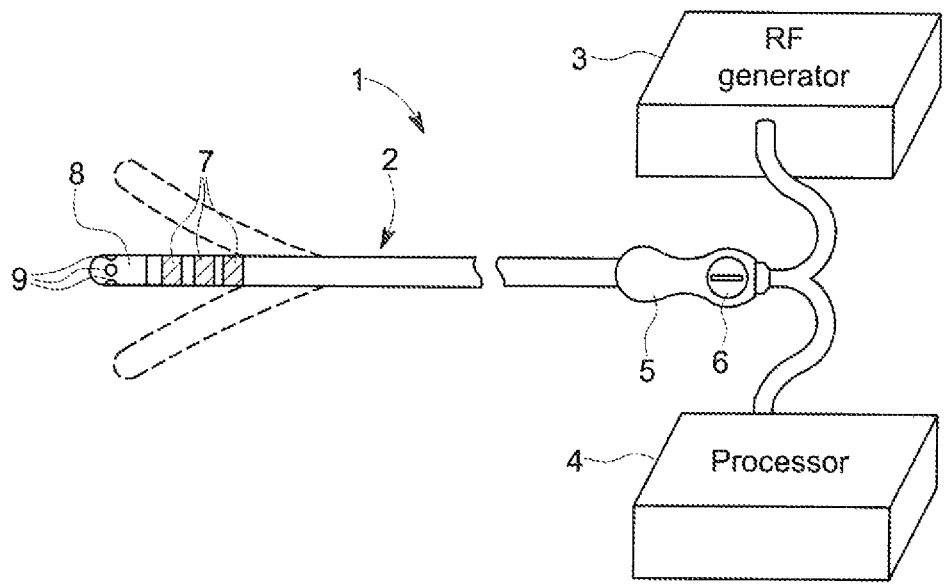
FIG. 1 is a schematic representation of a radio frequency (RF) ablation system according to an exemplary embodiment of the invention.

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Further, the foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

FIG. 1 is a schematic illustration of an electrophysiology system, e.g., a radio frequency (RF) ablation system 1 according to one embodiment of the invention, such as that disclosed in U.S. Pat. No. 8,876,817, entitled "ELECTROPHYSIOLOGY SYSTEM AND METHODS", which is expressly incorporated herein by reference for all purposes. As shown in FIG. 1, the system 1 includes an ablation catheter 2, an RF generator 3, and a processor 4. The ablation catheter 2 is operatively coupled to both the RF generator 2 and the processor 4, as will be described in greater detail herein. As further shown, the ablation catheter 2 includes a proximal handle 5 having a control knob 6, a flexible body having a distal portion including a plurality of ring electrodes 7, a tissue ablation electrode 8, and a plurality of microelectrodes 9 (also referred to herein as "pin" electrodes) disposed within and electrically isolated from the tissue ablation electrode 8. Each microelectrode 9 is also separately connected to the processor 4 by a connection 10, e.g., a wire, extending between the microelectrode 9 and the processor 4 along the catheter 2.

In various embodiments, the ablation catheter 2 is configured to be introduced through the vasculature of the patient, and into one of the chambers of the heart, where it can be used to map and ablate myocardial tissue using the microelectrodes 9 and the tissue ablation 8. Thus, the tissue ablation electrode 8 is configured to apply ablation energy to the myocardial tissue. In the illustrated embodiment, the ablation catheter 2 is steerable, such that the distal portion can be deflected (as indicated by the dashed outlines in FIG. 1) by manipulation of the control knob 6. In other embodiments, the distal portion of the ablation catheter 2 has a pre-formed shape adapted to facilitate positioning the tissue ablation electrode 8 and the microelectrodes 9 adjacent to specific target tissue. In one such embodiment, the pre-formed shape is generally circular or semi-circular and is oriented in a plane transverse to the general direction of the catheter body.

Figure 2:
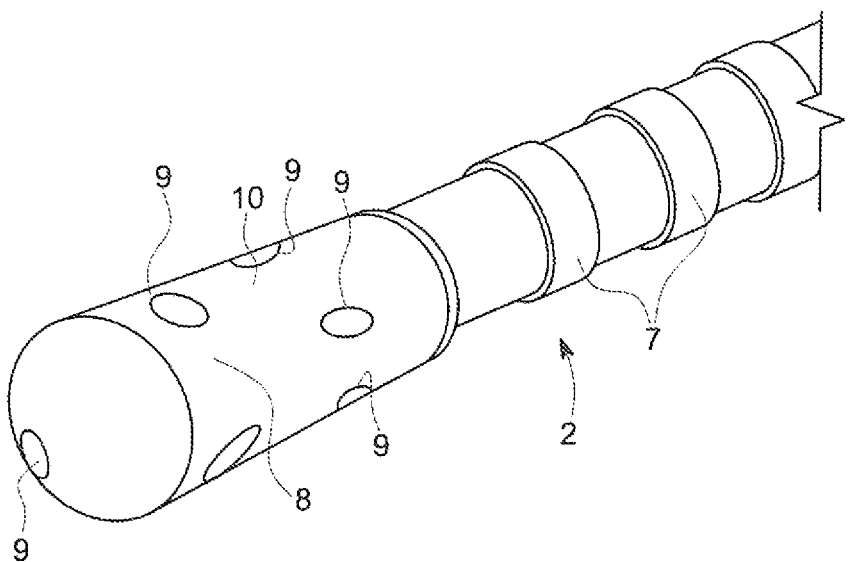
FIG. 2 is a schematic view of a high-resolution ablation catheter including microelectrodes disposed on the ablation electrode according to an exemplary embodiment of the invention.

In various embodiments, such as shown in FIGS. 1 and 2, the microelectrodes 9 are circumferentially distributed about the tissue ablation electrode 8 and electrically isolated therefrom. The microelectrodes 9 can be configured to operate in unipolar or bipolar sensing modes. In various embodiments, the plurality of microelectrodes 9 define a plurality of bipolar microelectrode pairs, each bipolar microelectrode pair being configured to generate an output signal corresponding to a sensed electrical activity of the myocardial tissue proximate thereto. The generated output signals from the microelectrodes 9 can be sent to the mapping processor 4 for processing as described herein.

Figure 3:
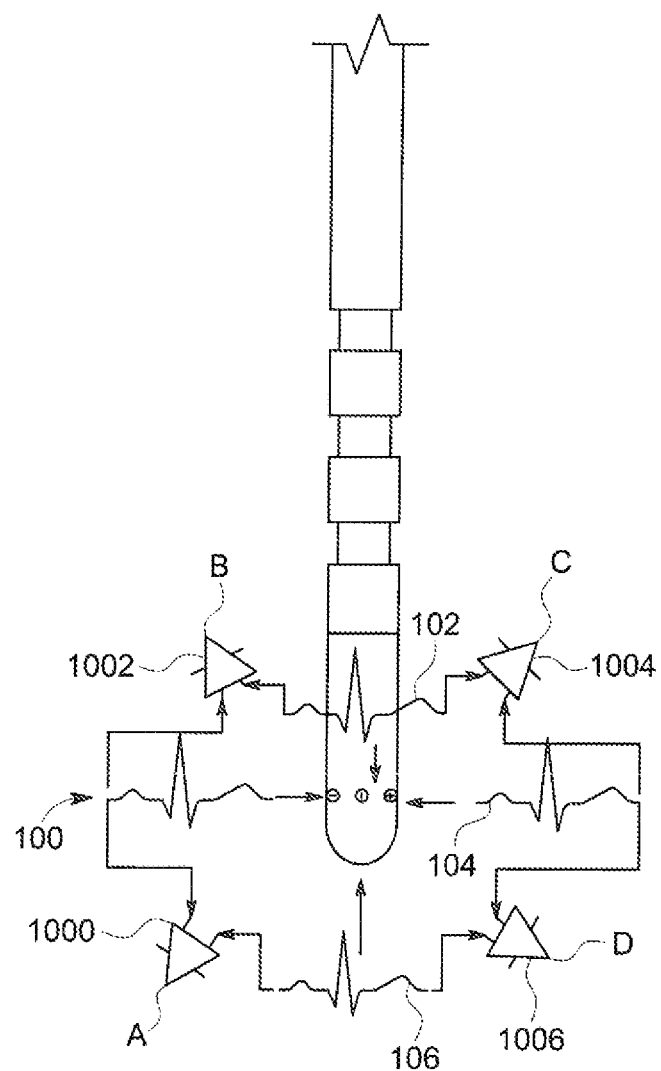
FIG. 3 is a schematic view of the catheter of FIG. 2 illustrating the signals obtained by the various microelectrodes disposed on the catheter and the comparative analysis of the adjacent signals according to another exemplary embodiment of the invention.
Figure 4:
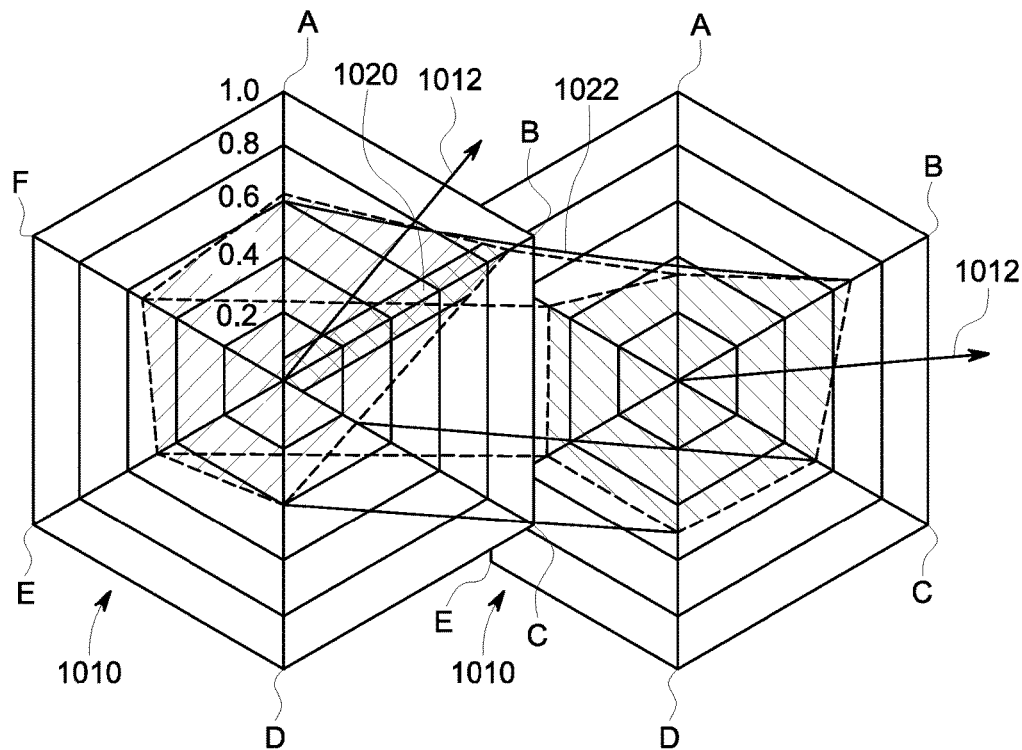
FIG. 4 is a schematic view of a representative displayed visual analysis of the comparative analysis of the adjacent signals according to another exemplary embodiment of the invention.

Exemplary catheters that can be used as the ablation catheter 2 can include those described in U.S. Patent App. Pub. Nos. US2008/0243214 entitled "High Resolution Electrophysiology Catheter," and US2010/0331658, entitled "Map and Ablate Open Irrigated Hybrid Catheter," which are hereby incorporated by reference in their entireties for all purposes. In various exemplary embodiments, the tissue ablation electrode 8 can have a length of between six (6) and fourteen (14) mm, and a plurality of microelectrodes 9 equally spaced about the circumference of the tissue ablation electrode 8. In one embodiment, the tissue ablation electrode 8 can have an axial length of about eight (8) mm. In one exemplary embodiment, the ablation catheter 2 includes at least two (2) but optionally three (3) microelectrodes 9 equally spaced about the circumference of the tissue ablation electrode 8 and at the same longitudinal position along the longitudinal axis of the tissue ablation electrode 8, the microelectrodes 9 forming at least first, second and third bipolar microelectrode pairs. In one exemplary embodiment, the catheter 2 includes a forward-facing microelectrode 9 generally centrally-located within the tissue ablation electrode 8, e.g. the tip of the ablation electrode 8. An exemplary such RF ablation catheter is illustrated in FIGS. 3 and 4 of the aforementioned U.S. Patent Application Pub. No. US2008/0243214.

In some exemplary embodiments, microelectrodes 9 can be located at other positions along the ablation catheter 2 in addition to or in lieu of the microelectrodes 9 in the tissue ablation electrode 8. In still other embodiments, the ablation catheter 2 can include up to "n" microelectrodes 9 spaced around the circumference of the ablation electrode 8, with "n" defined as the maximum number of axial microelectrodes 9 that can be equidistantly spaced around the longitudinal central axis of the ablation catheter 2 in relation to the size of the microelectrodes 9 being utilized.

In various exemplary embodiments, the tissue ablation electrode 8 has an exterior wall that defines an open interior region (not shown). The exterior wall includes mapping electrode openings for accommodating the microelectrodes 9, and, in some embodiments, irrigation ports (not shown). The irrigation ports, when present, are in fluid communication an external irrigation fluid reservoir and pump (not shown) for supplying irrigation fluid to the myocardial tissue being mapped and/or ablated. Exemplary irrigated catheters for use as the catheter 2 can be any of the catheters described in the aforementioned U.S. Patent App. Pub. No. 2010/0331658. In various exemplary embodiments, the catheter system may also include noise artifact isolators (not shown), wherein the microelectrodes 9 are electrically insulated from the exterior wall by the noise artifact isolators.

The RF generator 3 is configured to deliver ablation energy to the ablation catheter 2 in a controlled manner in order to ablate the target tissue sites identified by the mapping processor 4. Ablation of tissue within the heart is well known in the art, and thus for purposes of brevity, the RF generator 3 will not be described in further detail. Further details regarding RF generators are provided in U.S. Pat. No. 5,383,874, which is expressly incorporated herein by reference. Although the mapping processor 4 and RF generator 3 are shown as discrete components, they can alternatively be incorporated into a single integrated device.

The RF ablation catheter 2 as described may be used to perform various diagnostic functions to assist the physician in an ablation treatment. For example, in some embodiments, the catheter is used to ablate cardiac arrhythmias, and at the same time provide real-time assessment of a lesion formed during RF ablation. Real-time assessment of the lesion may involve any of monitoring surface and/or tissue temperature at or around the lesion, reduction in the electrocardiogram signal, a drop in impedance, direct and/or surface visualization of the lesion site, and imaging of the tissue site (e.g., using computed tomography, magnetic resonance imaging, ultrasound, etc.). In addition, the presence of the microelectrodes within the RF tip electrode can operate to assist the clinician in locating and positioning the tip electrode at the desired treatment site, and to determine the position and orientation of the tip electrode relative to the tissue to be ablated.

In various exemplary embodiments, the mapping processor 4 is configured to detect, process, and record electrical signals within the heart via the ablation catheter 2. Based on these electrical signals, a physician can identify the specific target tissue sites within the heart, and ensure that the arrhythmia causing substrates have been electrically isolated by the ablative treatment. The processor 4 is configured to process the output signals from the microelectrodes 9 and/or the ring electrodes 7, and to generate an output to a display (not shown) for use by the physician. In some exemplary embodiments, the display can include electrocardiograms (ECG) information, which can be analyzed by the user to determine the existence and/or location of arrhythmia substrates within the heart and/or determine the location of the ablation catheter 2 within the heart. In various exemplary embodiments, the output from the processor 4 can be used to provide, via the display, an indication to the clinician about a characteristic of the ablation catheter 2 and/or the myocardial tissue being mapped.

In addition to a mapping function of the processor 4, the processor 4 utilizes the signals obtained from the axial microelectrodes 9 to define the orthogonality of the ablation electrode 8 relative to the tissue. In looking at the exemplary embodiment illustrated in FIGS. 3 and 4, the output signals 100, 102, 104, 106, such as ECG signals, obtained from the microelectrodes 9, such as the three (3) microelectrodes 9 spaced around the circumference of the ablation electrode 8 and the one (1) microelectrode 9 disposed in the tip of the ablation electrode 8 in the exemplary embodiment in FIG. 3, are routed to analog or digital morphology comparators 1000, 1002, 1004, 1006 in order to provide difference signals A, B, C, D representative of the comparisons of the various signals 100, 102, 104, 106 from adjacent microelectrodes. In the exemplary embodiment, the comparators 1000, 1002, 1004, 1006 compare the signals 100, 102, 104, 106 obtained at the same particular instance of time to determine whether the compared signals 100, 102, 104, 106 are an exact match (having a representative value of 1) or are not an exact match (having a representative value of 0). The values for the difference signals A, B, C, D are then analyzed to provide an indication of the orthogonality of the ablation electrode 8 relative to the tissue in which the ablation electrode 8 is disposed.

Figure 5:
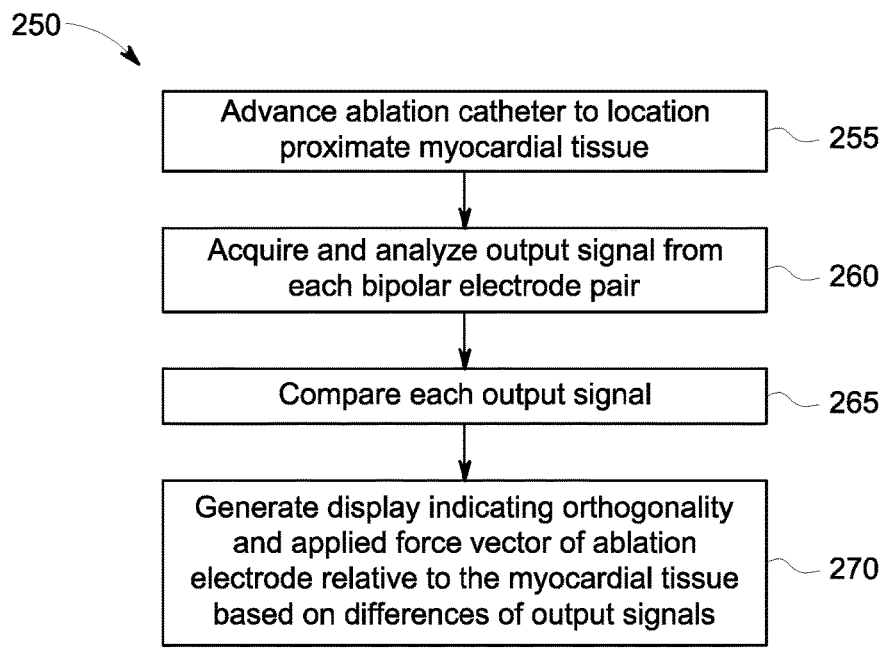
FIG. 5 is schematic view of the process of the operation of the system of FIG. 1 according to another exemplary embodiment of the invention.

In an exemplary embodiment, the method 250 of analysis of the difference signals by the processor 4 as illustrated in FIG. 5 is utilized to generate a wire frame space plot 1010 illustrated in FIG. 4 that can be visually represented on a display associated/operably connected to the processor 4. In the exemplary embodiment of FIG. 4, after positioning the ablation electrode 8 within the tissue, in block 255, six (6) electrodes 9 are present in the ablation electrode 8, providing six (6) signals 100, 102, 104, 106, 108, 110 to the processor 4 in block 260. Pairs of these signals 100, 102, 104, 106, 108, 110 are supplied to associated comparators (not shown) in order to derive difference signals A, B, C, D, E, F in block 265. The difference signals A, B, C, D, E, F are analyzed in block 270, e.g., averaged, and represented at each of the vertices/poles of the plot 1010 with the analysis results for the difference signals A, B, C, D, E, F represented by the shaded area 1011 of the plot 101 in order to indicate the angle of the ablation electrode 8/catheter 2 relative to the tissue as well as the force applied to the ablation electrode 8/catheter 2 by the tissue. In the exemplary plot 1010 of FIG. 4, the shaded area 1011 indicated that the portion(s) of the ablation electrode 8 represented by difference signals A, B and F are in significant contact with the surrounding tissue, while the portions represented by difference signals C-E are in much less contact with the tissue.

This visualization employing the wire frame plot 1010 can work with any of the three alternate methods of force sensing utilized in catheters 2—mechanical stiffness, impedance and optical methods. The wire frame space model/plot 1010 utilizes "n" nodes where in each node relates to a sensing electrode 9, regardless of physical technology. As a result, the shape and resolution of the wire frame space plot 1010 tends to a circular shape as the number of electrodes 9 increases, with the plot 1010 taking various geometric shapes depending on the number of electrodes 9 actually present in the ablation electrode 8. For example, in the exemplary embodiment of the catheter 2 of FIGS. 1-3, the plot 1010 will realize as a triangle, while the plot 1010 in the exemplary embodiment of FIG. 4, where six (6) microelectrodes are present, realizes as a hexagon.

Additionally, the processor 4 can apply a vector analysis to the signals 100, 102, 104, 106, etc. and/or on the difference signals A, B, C, D, etc. from the "n" electrodes 9 present on the catheter 2 to determine a region of interest (ROI) by peak signal analysis for each derived lead/electrode 9 at a given instance of time. Applying an averaging function to this vector analysis determines a vector of consistently greatest value in order to provide a localized axis from which the focus of the study can be determined. The focus may be determined by vector calculation of path to peak level or earliest activation, for example. In addition, this process can be automated such that the analysis will be performed by the processor 4 without any required user intervention as the signals 100, 102, 104, 106, etc. and/or on the difference signals A, B, C, D, etc. are received and/or calculated by the processor 4. Additionally, this process can then be utilized to sequence/represent the best view of the plot 1010 on the display (not shown) relative to other channels that are set to be displayed for each vector view providing a sequenced or triggered view relative to the signal processed vector. Other functions that can also be associated and triggered with this process include gain increase of select channels and change of trace color on the signals nearest to the reference vector, among others. Additionally, the area inside the curve can be color-coded and/or shaded to represent other information provided by the signals, such as the percent of the colored/shaded area in the plot that is proportional to orthogonality.

Each pole or vertex of the wire frame plot 1010 can be further convolved with additional parametric information, such as impedance measurements or electrical current conduction, to represent the angulation of the ablation electrode 8 through distortion of the wire frame. This information can be deduced from the screen presentation of the wire frame plot 1010, and/or through a computer derived line representing the overall applied force vector/axis 1012 illustrated on the plot 1010 where force is proportional to the colored/shaded area of the wire plot 1010. Energy applied to the ablation catheter and through applied force can also be translated to a visual shading scheme on or within the wire frame plot 1010, which can be further sub-shaded relative to the pole or vertex of the plot 1010 representing the greatest force vector (e.g., the pole corresponding to difference signal B in FIG. 4). Additionally, the average applied pressure may also be calculated for the entire surface of the ablation catheter 8 using the force vector values determined for each pole of the plot 1010, e.g., the values for each of the difference signals (e.g., values A-F in FIG. 4).

In another exemplary embodiment, additional orthogonal microelectrodes 9 can be positioned within the ablation electrode 8 spaced from the microelectrodes 9 opposite the tip of the ablation catheter 8, in order to provide the catheter 2 with the ability to represent a depth x of the ablation electrode 8 relative to the tissue. The depth x has a number of layers y identified by each array or set of microelectrodes 9 such that the ablation catheter force, and "depth" of insertion within the muscle/heart or other tissue can be determined as before. However, the measurements made can now be repeated for each layer y relative to available depth x, and represented on the screen via multiple wire frame plots 1010/vectors 1012. Applying the principles developed previously the user can display an aggregated view, or switch between layers y such that the overall performance of the system 1 can be evaluated and the depth of insertion into the tissue can be similarly deduced.

Further, this method for generating the display/plot 1010 can be applied to a different type of catheter 2 including an ablation electrode 8 configured to create linear burns versus the described spot burns, such as the nMarq linear catheter developed by Biosense Webster or Phased RF Catheter PVAC, MAAC and MASC specialist catheters made by Medtronic. In an as-is model using this type of catheter 2, the system 1 can generate the wire frame plots 1010 in the aforementioned manner which can then be stacked to represent the applied energy from the catheter 2. In another exemplary embodiment, a modification of the catheter 2 uses impedance sensing electrodes (not shown) inserted axially along the median of the ablation electrode 8/catheter 2 at periodic intervals. In this configuration, contact impedance can be triangulated between the electrodes relative to the ablation electrode 8 to allow applied force to be determined.

Further, in still another exemplary embodiment a multi-dimensional stack of wire frame space plots 1010 (FIG. 4) can be developed to allow the user to better monitor the overall performance of the catheter 2 relative to the desired tissue pathology and/or tissue changes that are desired. The wire frame space plots or models 1010 obtained from the microelectrodes 9 can be layered in a known manner to overlap and join the shaded areas 1011 using the known spacing of the sets/arrays of microelectrodes 9 forming each shaded area 1011 to provide a three-dimensional (3D) representation or image of the tissue contacted by the catheter 2, both before the catheter 2 is operated and after a burn has been performed using the catheter 2, such as in the performance of a percutaneous coronary intervention (PCI). In this manner, the three-dimensional (3D) image constructed via the layered plots 1010 obtained using signals from the microelectrodes 9 can show the isolation achieved in the tissue as a result of the 3D images of the tissue taken before and after the burn, such as by an overlapped, collated, correlated and/or comparative 3D image of the before and after tissue structure(s). This process using the catheter 2 including the spaced arrays of microelectrodes 9 can also be employed when performing a pulmonary vein isolation (PVI), or a pulmonary vein antral isolation (PVAI). Some exemplary embodiments of this pathology correlation are known in the art, such as Lesion Size Index (LSI) which provides a numerical estimation of cautery effect.

In summary, some of the technical advantages of the system 1 and method 250 of the invention include:
1. The system 1 and method 250 use wire frame plots 1010/visualization technology allowing scalable solution from two (2) or three (3) to n electrodes 9.

2. The system 1 and method 250 can be utilized independent of the type of technology employed in the catheter 2 to sense force.
3. The system 1 and method 250 are capable of multivariant information representation.
4. The system 1 and method 250 are scalable beyond one layer y.
5. The system 1 and method 250 are 3D representation capable.
6. The system 1 and method 250 can support a single contact burn catheter, and multipole devices for specialist or linear burns.

In summary, some of the commercial advantages of the system 1 and method 250 of the invention include:
1. The system 1 and method 250 can be employed independent of ablation catheter technology.
2. The system 1 and method 250 enable advanced procedures using complex ablation catheters.
3. The system 1 and method 250 provides axis of force analysis, convolved with applied power to provide visual metaphor for resultant tissue transformation.
4. The system 1 and method 250 provides for multi-polar ablation catheters.
5. The system 1 and method 250 provides for depth of burn monitoring.
6. Catheters 2 used in the system 1 and method 250 may be substantially less expensive than state of the art mechanical force sensing catheters.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for determining the orthogonality and applied force vector of an ablation catheter, the method comprising the steps of:
   providing an electrophysiology system including an RF generator; a processor operably connected to the RF generator; a display operably connected to the processor and an ablation catheter operably connected to the RF generator and the processor, the catheter including an ablation electrode disposed opposite the RF generator and forming a tip of the ablation catheter and a number of microelectrodes disposed on and electrically isolated from the ablation electrode, the processor configured to compare data signals obtained from the microelectrodes with one another to derive a difference value for each pair of data signals;
   positioning the ablation electrode within the tissue to be ablated;
   obtaining data signals from the microelectrodes;
   comparing the data signals from microelectrode pairs to determine difference values; and
   generating a visual representation on the display of the orthogonality and an applied force vector of the ablation electrode relative to the tissue using the difference values,
   wherein the step of generating the visual representation comprises generating a wire form space plot, wherein the ablation electrode provided includes a number of sets of spaced microelectrodes,
   wherein the step of generating the visual representation comprises generating a wire form space plot for each set of microelectrodes, and
   wherein the step of generating a wire form space plot for each set of microelectrodes further comprises generating a three-dimensional representation of the tissue using the wire form space plots.

2. The method of claim 1 wherein the step of generating a three-dimensional representation of the tissue using the wire form space plots comprises layering the wire form space plots to form a three-dimensional image of the tissue.

3. The method of claim 2 wherein the step of generating the three-dimensional representation of the tissue comprises the steps of;
   generating a three-dimensional image of the tissue prior to performing an ablation on the tissue; and
   generating a three-dimensional image of the tissue after performing an ablation on the tissue.

4. The method of claim 3 further comprising the step of combining the three-dimensional images prior to ablation with the three-dimensional image after ablation to form an overlapped, collated, correlated and/or comparative 3D image of the tissue structure(s).

* * * * *